United States Patent [19]

Altman

[11] 4,252,793
[45] Feb. 24, 1981

[54] INJECTABLE LECITHIN PREPARATION

[75] Inventor: Reinout F. A. Altman, Rio De Janeiro, Brazil

[73] Assignee: American Lecithin Company, Atlanta, Ga.

[21] Appl. No.: 49,122

[22] Filed: Jun. 18, 1979

[51] Int. Cl.³ .................... A01N 57/26; A61K 31/685
[52] U.S. Cl. .................................. 424/199; 260/403; 252/356
[58] Field of Search ....................... 424/199; 260/403; 252/356

[56] References Cited

U.S. PATENT DOCUMENTS

| | | | |
|---|---|---|---|
| 1,741,786 | 12/1929 | Magat | 424/199 |
| 2,185,969 | 1/1940 | Schultze | 424/199 |
| 3,203,862 | 8/1965 | Jones | 424/199 |
| 4,005,190 | 1/1977 | Mader et al. | 424/199 |
| 4,174,296 | 11/1979 | Kass | 260/403 |

FOREIGN PATENT DOCUMENTS 725596  1/1966 Canada .................................. 424/199

OTHER PUBLICATIONS

Zilversmit, D. et al., J. of Lab. and Clin. Med., vol. 48, No. 3, pp. 386–391, Sep. 1956.

*Primary Examiner*—John F. Niebling
*Attorney, Agent, or Firm*—Louis T. Isaf

[57] ABSTRACT

A method of preparing an injectable preparation of lecithin including 1 to 10% lecithin comprises the steps of separately preparing a lecithin fraction including lecithin and a non-hydrous liquid, separately preparing an aqueous fraction containing a surfactant, and then combining the two fractions and manually shaking for twenty to thirty seconds. Beneficial medicaments are added to either the lecithin fraction or aqueous fraction prior to combining of the two.

6 Claims, No Drawings

INJECTABLE LECITHIN PREPARATION

TECHNICAL FIELD

The present invention relates to a method of preparing a water-based lecithin pharmaceutical whereby substantially water-free lecithin is introduced into an aqueous system and reduced to extremely fine particle size in a matter of seconds.

BACKGROUND OF THE INVENTION

Prior to the present invention, lecithin has been included, in only small amounts, as an emulsifier in emulsions for intravenous feeding of patients. Typically these emulsions for intravenous feeding are mediums for intravenously supplying quantities of vegetable oils and fats for nourishment to patients and the amount of lecithin found in these emulsions is generally one percent (1%) or less.

In recent years it has been found that lecithin is not only useful as an emulsifier, but lecithin also possesses valuable physiological properties of its own. Lecithin is involved in various enzyme systems and in the metabolism of lipids, in particular cholesterol because lecithin and other phospholipids have been repeatedly recognized as the natural antagonists of cholesterol in many physical, chemical and biological processes. This is of utmost importance since the human diet contains too often a large excess of cholesterol and saturated fats leading to an accentuated increase of Very Low and Low Density Lipoproteins (VLDL and LDL) in the blood plasma, causing various disturbances particularly atherosclerosis (formation of fatty or "antheromatous" plaques in the intima and media of arteries) and other cardiovascular diseases. As lecithin and other phospholipids, in stimulating the production of High Density Lipoproteins (HDL) in plasma and, thus, compensating whatever increase of VLDL and LDL, do in fact achieve the resolution of atheromatous plaques, it will be desirable to provide an efficient and convenient means for injecting effective amounts of lecithin into the human body to aid in the control of excess cholesterol and fats.

In preparing lecithin for injection into the human body, it is necessary that the injectable preparations containing the lecithin, which may also contain other suitable substances, be physiologically acceptable for injection into the human body. Also, it is desirable that the injectable preparations posses particles with sizes of less than three microns and it is preferable that 95% or more of the particles should measure one micron or less in diameter. Attempts to prepared suitable injectable lecithin preparations have been generally unsuccessful or, at least, unsatisfactory in the past.

Lecithin, for example, is difficult to emulsify in its dry state and does not readily emulsify in water without vigorous shaking and agitation. Furthermore, aqueous dispersions or emulsions of lecithin have limited shelf life and have been found to develop toxic properties after having been stored over a period of time.

SUMMARY OF THE INVENTION

Briefly described, the present invention comprises a method of preparing a dispersion or, if water insoluble substances such as fatty oils are present, an emulsion including substantial percentages of lecithin or other associated phospholipid material for injection or infusion into the human body.

The method of the present invention includes the step of dispersing or dissolving relatively large quantities of lecithin in a substantially anhydrous and non-toxic vehicle such as, for example, ethanol, glycerides including fatty acids, and liquid oils to provide an anhydrous lecithin fraction. An aqueous fraction is prepared separate from the lecithin fraction and includes one or more surface active agents dissolved therein. The lecithin fraction and aqueous fraction are prepared, packaged and sterilized separately. Shortly before time for injection of the patient with the lecithin, the lecithin fraction and aqueous fraction are mixed, Emulsification or dispersion occurs almost immediately after mixing with simple manual shaking of the mixture of the two fractions. Therefore, in accordance with the present invention, the lecithin fraction and aqueous fraction are combined to form the emulsion or dispersion for injection immediately prior to injection, that is, at the time of use.

It is desirable to include in the aqueous fraction a component which makes the injectable dispersion or emulsion isotonic, i.e. physiologically acceptable to the human body. This can be performed by, for example, glucose in a final concentration of 4% or sodium chloride in a final concentration of 0.9%. Furthermore, in accordance with the present invention, oil soluble vitamins and other oil soluble medicaments can be added to the lecithin fraction. Water soluble vitamins and other water soluble medicaments can be added to the aqueous fraction.

Therefore, it is an object of the present invention to provide injectable dispersions or emulsions prepared with substantial amounts of lecithin which are of fine particle size and free from toxicity or harmful side effects.

Another object of this invention is to facilitate the preparation of emulsions or dispersions including substantial amounts of lecithin for injection or infusion by providing a separate, stable lecithin-containing phase and a separate stable aqueous phase.

A further object is to provide convenient to use, freshly prepared lecithin-containing pharmaceutical dispersions or emulsions of fine particle size and excellent stability including substantial amounts of lecithin.

A still further object of this invention is to provide for the preparation of a phospholipid emulsion or dispersion including substantial amounts of lecithin or lecithin rich phospholipid immediately prior to administration by injection or diffusion.

Still another object of the invention is to maintain a lecithin or lecithin containing product in a substantially non-deteriorating, quickly dispersible or emulsifiable form for convenient use with an aqueous phase immediately before injection.

Other objects, features and advantages of the present invention will become apparent upon reading the following specification.

DETAILED DESCRIPTION

More precisely described, the method of the present invention comprises the steps of separately mixing an anhydrous mixture including substantial amounts of lecithin, called the lecithin fraction, and an aqueous mixture including a suitable surfactant, called the aqueous fraction. The two separate fractions are packaged separately and are sterilized separately, preferably after packaging, and stored until needed. Immediately prior to injection or infusion, the lecithin fraction and aqueous fraction are combined resulting, after manual agitation, in a dispersion or emulsion suitable for injection.

The lecithin, or a lecithin-containing phospholipid, of the lecithin fraction is, per se, substantially anhydrous, usually with less than 1.5% moisture. A non-toxic liquid medium is combined with the lecithin in the lecithin fraction and this liquid medium is also substantially anhydrous. Examples of suitable anhydrous liquid mediums are absolute ethanol (although less desirably it is possible to use 95% ethanol), liquid mono- or diglycerides, essential fatty acids, oils such as soybean oil, cottonseed oil, corn oil, safflower oil and the like. The lecithin-containing phospholipids are those normally associated with lecithin in nature such as phosphatidyl ethanolamine and phosphatidyl inositol. The amount of lecithin contained in the lecithin fraction preferably ranges from 10% to 80% by weight of the lecithin fraction. Liquids which have been shown to be potentially toxic when given intravenously should be avoided.

The aqueous fraction comprises water with non-toxic, physiological surfactants dissolved therein which promote dispersion and emulsification of lecithin. The aqueous fraction may serve as a carrier for other substances also. Surfactants which are used in accordance with the present invention include the block polymers of ethyleneoxide and propyleneoxide with the general formula: $HO(CH_2CH_2O)a[CH(CH_3)CH_2O]b(CH_2CHO)c$ H and a molecular weight of 3,000 or more. The letters, a, b, and c, of the above formula represent whole numbers which identify the number of units of the organic composition preceeding the respective a, b, or c. The whole number represented by a, b, or c may vary according to the stability of the respective compound in oil or water. If the chain length of the hydrophilic units (polyoxyethylene) and hydrophobic units (polyoxypropylene) are increased, the product changes from liquid to paste to solid with increasing mol. wt. (cf. U.S. Pat. No. 2,674,619 to Wyandotte Chemical Corp., 1954). These block polymers of the above formula include, for example, block polymers known under the trademarks "Pluronics" or "Poloxalenes" or "Polykols". Pluronic F-68 represents one of the solid members of this group of surfactants and is preferred for use in the present invention due to its extreme purity and solubility in water. Other surfactants applicable are sodium cholate, dioxycholic acid and the sodium soaps of preferably unsaturated fatty acids which are better soluble in water than the soaps of saturated fatty acids. The amount of surfactant used depends upon its effectiveness and generally ranges from 0.1% to 1.0% by weight of the aqueous fraction.

Upon conbination of the lecithin fraction and aqueous fraction, a fluid preparation, i.e., dispersion or emulsion, suitable for infusion or injection into the human body, results. In the presence of fatty oils and the like which are insoluble in water, an oil-in-water emulsion is formed rather than a dispersion or colloidal solution and the amount of lecithin or lecithin rich phospholipid could vary from 5% to 15% of the weight of the oil. The oil in an emulsion for intravenous alimentation would amount to about 10% to 15% of the emulsion, glucose or saline usually being included in the aqueous phase along with the surfactant. Glucose at a final concentration of about 4% or sodium chloride at a final concentration of about 0.9%, or like substances which improve the isotonic properties of the final injectable preparation are added, as necessary, in the aqueous fraction to aid in making the final injectable preparation physiologically acceptable to the human body.

Preferably, the injectable preparation resulting, in accordance with the present invention, from the combining of the lecithin and aqueous fractions comprises approximately 1% to 10% lecithin by weight and the particles within the injectable preparation range in size from less than one micron to five microns. The injectable dispersion or emulsion occurs within approximately 20–30 seconds with only simple manual shaking of the combined fractions required.

Preferably, to comprise the lecithin fraction, lecithin or lecithin-containing phospholipid is dissolved in absolute alcohol changing at will the lecithin concentration from 50% to 80% by weight, which means that the proportion lecithin:alcohol may vary from 1:1 to 4:1. An aqueous fraction comprising water containing approximately 0.3% pluronic F-68 is prepared and packaged separately from the lecithin fraction. The lecithin fraction and the aqueous fraction are sterilized separately, for example by autoclaving, without danger of decomposition and are stored separately for as long a period necessary before time for use. Immediately prior to the time of use, the lecithin fraction is mixed with the aqueous fraction. Preparation of the emulsion or dispersion at the time of use guarantees that the patient always receives freshly prepared emulsions. A convenient form for injection comprises a lecithin fraction containing 0.8 gram of a 60% lecithin solution in absolute alcohol, separately packaged, and 4.2 grams of an also separately packaged aqueous fraction comprising a solution of 200 mg glucose, 150 mg glycerol and 15 mg pluronic F-68. When the two fractions are mixed together, an injectable emulsion results after approximately 20 seconds of manual shaking, including 10% lecithin by weight and including particles, all of which are less than approximately 3 microns.

Oil soluble vitamins and other oil soluble medicaments can be added to the lecithin fraction and water soluble vitamins and other water soluble medicaments can be added to the aqueous fraction. Preferably, vitamins and medicaments are injected in conjunction with polyunsaturated soybean phospholipids, especially those fractions rich in phosphatidyl choline.

In the case of vitamin C for example it has been found in conjunction with the present invention that, given simultaneously with lecithin, vitamin C enhances the effectiveness of the lecithin and vice versa. Thus, in one series of tests with adult rabbits on an atherogenic diet, the lecithin was given by administering 5 ml of a 10% aqueous dispersion, made in accordance with the present invention, of soybean phospholipid containing about 60% lecithin (phosphatidyl choline) and 100 mg of vitamin C orally as a 10% solution. An examination of heart and aorta after three months showed extensive atheromatous plaques in the controls, very much less in the animals receiving lecithin and those receiving vitamin C and in the rabbits receiving both lecithin and vitamin C the heart and aorta were completely free of atheromatous plaques. Various other medicaments which can be added to either the lecithin or aqueous fractions in order to be beneficially injected with the lecithin preparation include: sphingomyelin phospholipid, albumin, glycerol, procaine dihydrate, linoleic acid, Vitamins A, C, E, Vitamins B-12, B-1, the uses of which are pointed out in various of the examples below.

EXAMPLE I

A lecithin fraction is separately packaged comprising 625 mg of an 80% solution of lecithin or lecithin rich phospholipid in substantially absolute ethanol. An aqueous fraction is separately packaged comprising 4.375 grams of an aqueous solution of 200 mg glucose, 150 mg glycerol and 15 mg Pluronic F-68. After separate sterilization, the lecithin fraction and aqueous fraction are mixed and shaken vigorously by manual shaking for 20 to 25 seconds shortly before intravenous application to form a dispersion suitable for injection. The resulting dispersion suitable for injection into the human body includes approximately 10% lecithin and all particles are less than 3 microns in size.

EXAMPLE II

A lecithin fraction is separately packaged comprising 625 mg of an 80% lecithin solution in absolute alcohol and 75 mg of crystalline injectable vitamin C. An aqueous fraction is separately packaged comprising 4.3 grams of an aqueous solution of 200 mg glucose, 150 mg glycerol and 15 mg Pluronic F-68. After separate sterilization, the lecithin fraction and the aqueous fraction are mixed and manually shaken vigorously for 25 seconds shortly before intravenous application to form a dispersion suitable for injection. This dispersion with particles of less than 5 microns in size, contains 10% lecithin and 1.5% vitamin C.

EXAMPLE III

A lecithin fraction is separately packaged comprising 500 mg lecithin and 100 mg sphingomyelin dissolved in one ml absolute alcohol. An aqueous fraction is separately packaged comprising 240 mg glucose, 300 mg albumin and 18 mg Pluronic-F68 dissolved in 5 ml of water. After separate sterilization, the lecithin fraction and the aqueous fraction are mixed and shaken vigorously by hand for 20 seconds shortly before intravenous application to form a dispersion suitable for injection. The presence of sphingomyelin and albumin not only promotes dispersion of the mixture, but also has a favorable influence on the efficiency of the injection. The dispersion with particles of less than 3 microns in size, contains approximately 8.3% lecithin, 1.7% sphyngomyelin, and 5% albumin.

EXAMPLE IV

A lecithin fraction is separately packaged comprising 625 mg of an 80% solution of lecithin in absolute alcohol. An aqueous fraction is separately packaged comprising 4.375 grams of an aqueous solution of 200 mg glucose, 100 mg procaine dihydrate and 20 mg sodium cholate, the procaine component acting as an efficient geriatric. After separate sterilization, the lecithin fraction and the aqueous fraction are mixed and shaken vigorously by hand for 30 seconds shortly before intravenous application to form a dispersion suitable for injection. This dispersion with particles of less than 3 microns in size, contains 10% lecithin and 2% procaine dihydrate and is indicated for old persons suffering from atherosclerosis.

EXAMPLE V

A lecithin fraction is separately packaged comprising 625 mg of an 80% solution of lecithin in absolute alcohol and 75 mg pure linoleic acid. An aqueous fraction is separately packaged comprising 4.5 g of an aqueous solution of 200 mg glucose and 25 mg sodium oleate. After separate sterilization, the lecithin fraction and the aqueous fraction are mixed and manually shaken for 30 seconds shortly before intravenous application to form an emulsion suitable for injection. This emulsion with particles of less than 3 microns in size, contains 10% lecithin and 1.5% linoleic acid, the latter component, being one of the principal essential fatty acids, acts favorably in the prophylaxis and treatment of atherosclerosis.

EXAMPLE VI

A lecithin fraction is separately packaged comprising 500 mg lecithin, 10 mg vitamin A and 10 mg vitamin E, dispersed in 3 ml corn oil or other essential fatty oil. An aqueous fraction is separately packaged comprising 16.5 ml of an aqueous solution of 800 mg glucose, 60 mg Pluronic F-68, 10 mg vitamin B1 and 100 micrograms vitamin B12. After separate sterilization, the lecithin fraction and the aqueous fraction are mixed and manually shaken for 30 seconds shortly before intravenous application to form an emulsion suitable for injection. This emulsion with particles of less than 5 microns in size may be applied in atherosclerotic patients suffering from weakness and vitamin deficiency.

EXAMPLE VII

A lecithin fraction, separately packaged, comprises 3 g of cottonseed oil and 320 mg of a 75% lecithin solution in absolute alcohol. An aqueous fraction is separately packaged comprising 16.2 ml water in which 800 mg glucose and 60 mg Pluronic F-68 are dissolved. After separate sterilization, the lecithin fraction and the aqueous fraction are mixed and vigorously shaken manually for 30 seconds shortly before intravenous application to form an emulsion suitable for injection. The emulsion, which may be enriched with oil soluble and/or water soluble vitamins, serves for intravenous alimentation. The emulsified fat particles are less than 5 microns in size.

EXAMPLE VIII

A lecithin fraction, separately packaged, comprises 500 mg lecithin dispersed in 4.5 g dioleylglyceride. An aqueous fraction is separately packaged comprising 15 ml water in which 180 mg sodium chloride and 60 mg Pluronic-F68 are dissolved. After separate sterilization, the lecithin fraction and the aqueous fraction are mixed and vigorously shaken by hand for 30 seconds shortly before intravenous application to form an emulsion suitable for injection. The emulsified dioleylglyceride particles are less than 5 microns in size.

EXAMPLE IX

A lecithin fraction, separately packaged, comprises 500 mg lecithin and 10 mg beta carotene dispersed in 4.5 soybean oil. An aqueous fraction, separately packaged, comprises 15 ml water in which are dissolved 800 mg glucose and 100 mg sodium oleate. After separate sterilization, the lecithin fraction and the aqueous fraction are mixed and manually shaken for 30 seconds in order to form an emulsion suitable for intravenous injection. The emulsified particles are less than 5 microns in size.

EXAMPLE X

A lecithin fraction, separately packaged, comprises 625 mg of an 80% lecithin solution in absolute alcohol dispersed in 3 g safflower oil. An aqueous fraction, separately packaged, comprises 16.5 ml water in which are dissolved 180 mg sodiumchloride and 100 mg sodiumoleate. After separate sterilization, lecithin and aqueous fractions are mixed by manual shaking for 30 seconds to form an emulsion for injection. The emulsified oil particles are less than 5 microns in size.

While this invention has been described in specific detail with particular reference to preferred embodiments thereof, it will be understood that variations and modifications can be effected within the spirit and scope of the invention as described hereinbefore and as defined in the appended claims.

I claim:

1. Method of providing lecithin intravenously into the human body, comprising the steps of:
   preparing an anhydrous mixture including approximately 10% to 80% lecithin by weight and an anhydrous liquid selected from the group consisting essentially of ethanol, monoglycerides, diglycerides, fatty acids and liquid fatty oils;
   preparing an aqueous mixture including water and a surfactant selected from the group consisting essentially of block polymers of ethyleneoxide and propyleneoxide, sodium cholate, dioxycholic acid and soaps;
   separately packaging the anhydrous mixture and the aqueous mixture;
   separately sterilizing the anhydrous mixture and the aqueous mixture; and
   combining the aqueous mixture and the anhydrous mixture prior to intravenous administration into the human body to form a non-toxic fluid preparation suitable for intravenous administration within thirty seconds after combining including 1% to 10% lecithin by weight and including particles ranging in size from less than one micron to five microns.

2. Method of claim 1, wherein the step combining the aqueous mixture and the anhydrous mixture includes the step of manually shaking the two mixtures after they have been combined.

3. Method of claim 1, further comprising the step of administering the fluid preparation intravenously into the human body immediately after forming of the non-toxic fluid preparation.

4. A method of preparing lecithin for injection or infusion intravenously into the human body, said method comprising the steps of:
   mixing lecithin with an anhydrous liquid to form a lecithin fraction comprising 10% or more lecithin by weight;
   packing the lecithin fraction;
   sterilizing the lecithin fraction;
   storing the lecithin fraction and combining the lecithin fraction with an aqueous phase including water forming an injectable preparation comprising greater than 1% lecithin by weight.

5. An anhydrous lecithin fraction capable of being sterilized and stored for long periods of time prior to combining with water for human injection, said lecithin fraction comprising an anhydrous liquid selected from the group consisting essentially of ethanol, monoglycerides, diglycerides, fatty acids and liquid fatty oils; and lecithin in an amount equal to 10% to 80% by weight of the total lecithin fraction.

6. The lecithin fraction of claim 5 further comprising oil soluble medicaments including oil soluble vitamins.

* * * * *